United States Patent [19]

Schmidt et al.

[11] Patent Number: 4,500,391
[45] Date of Patent: Feb. 19, 1985

[54] METHOD OF AND SYSTEM FOR REAL TIME DIFFERENTIAL PULSE DETECTION

[75] Inventors: John C. Schmidt, Baltimore; Clifton A. Sands, Oxon Hill; Donald N. Campbell, Timonium, all of Md.

[73] Assignee: Allied Corporation, Morristown, N.J.

[21] Appl. No.: 541,631

[22] Filed: Oct. 13, 1983

[51] Int. Cl.³ ............................................. G01N 27/48
[52] U.S. Cl. .................................... 204/1 T; 204/406; 204/411; 204/412; 204/415; 204/431; 340/632
[58] Field of Search ............... 204/406, 411, 412, 431, 204/432, 1 T, 415; 340/632

[56] References Cited

U.S. PATENT DOCUMENTS 4,340,885 7/1982 Chavis et al. ........................ 340/632
4,388,822 6/1983 Heller ............................ 340/632 X

OTHER PUBLICATIONS

D. G. Swartzfager, Anal. Chem., vol. 48, No. 14, pp. 2189-2192, Dec. 1976.

Primary Examiner—G. L. Kaplan
Attorney, Agent, or Firm—Robert M. Trepp; Bruce L. Lamb

[57] ABSTRACT

An electrochemical detection cell which includes, in the order named, a stack of components constituted by a first membrane, an electrode carrier having reference and counter electrodes thereon, a membrane support, an electrode carrier having a sensing electrode thereon, and a permselective membrane. Whatman filter papers are positioned between the sensing electrode and both the counter electrode and reference electrode, these being positionable in a central rectangular opening of the membrane support. The cell allows air or gas ambient to address the membranes and effects application of an electrolyte to space between the electrodes by, for example, a wick which extends between an electrolyte-containing reservoir and the Whatman filter papers. A system for detecting a gaseous agent uses the aforementioned detection cell coupled with circuitry capable of applying a fixed DC voltage bias to the reference electrode and superimposing a train of DC voltage pulses on the fixed bias. Further circuitry is coupled to and responsive to signals from the sensing electrode. This circuitry determines the difference between the sensing electrode signal at the end of each pulse minus that just before each pulse. The difference is proportional to the concentration of the test gas in the atmosphere adjacent to the sensor, and is a more specific and sensitive indication of the test gas concentration than prior art sensors.

24 Claims, 16 Drawing Figures

METHOD OF AND SYSTEM FOR REAL TIME DIFFERENTIAL PULSE DETECTION

BACKGROUND OF THE INVENTION

The invention relates to a method of gas detection using real time differential pulse detection ("RDPD"), to an electronic system for carrying out the method, and to an electrochemical detection cell which can be used in the system. Real time differential pulse detection (RDPD) is a modification of differential pulse voltammetry ("DPV").

Known analytical systems using conventional voltammetry maintain an accurate potential between the sensing and reference electrodes of an electrochemical sensing cell which may include, in addition to the sensing and reference electrodes, a counter electrode.

Examples of prior art electrochemical detection cells, which include a sensing electrode, a reference electrode and a counter electrode are illustrated in respective U.S. Pat. Nos. 3,776,832 and 3,925,183 to Oswin et al. entitled respectively "Electrochemical Detection Cell" and "Gas Detecting and Quantitative Measuring Device" and issued respectively Dec. 4, 1973 and Dec. 9, 1975. The electrodes are of a type which must be operated in a conventional voltammetry mode and, consequently, one cannot realize the advantages of RDPD techniques.

Another example of a known electrochemical detection cell, which includes an anode, a cathode and a reference electrode is disclosed in U.S. Pat. No. 4,201,634 to Stetter entitled "Method of Detection of Hydrazine" and issued May 6, 1980. In this instance, the sensing or working electrode includes a noble metal catalyst capable of electrooxidation of hydrazine bonded to a hydrophobic material. The electrodes are so configured that detection cells constructed as proposed have the same shortcomings as those disclosed in the Letters Patents to Oswin et al., supra; selectivity and sensitivity is limited.

Additional examples of electrochemical detection cells are disclosed and illustrated in the U.S. Pat. Nos. identified as follows:

| U.S. Letters Pat. No. 4,040,805 | Nelms et al. | August 9, 1977 |
| U.S. Letters Pat. No. 4,048,041 | David et al. | September 13, 1977 |
| U.S. Letters Pat. No. 4,227,984 | Dempsey et al. | October 14, 1980 |
| U.S. Letters Pat. No. 4,235,097 | Kring et al. | November 25, 1980 |
| U.S. Letters Pat. No. 4,271,121 | Diller et al. | June 2, 1981. |

A detailed discussion of the theory, techniques and waveforms used in conventional differential pulse voltammetry as used in laboratories can be found in Sawyer et al., *Experimental Electrochemistry for Chemists*, pages 280, 389-394, John Wiley & Sons, New york, N.Y. (1974) and in Skoog et al, *Fundamentals of Analytical Chemistry*, 3rd Edition, pages 492-494, Sanders College, Philadelphia, Pa. (1976). In this known technique, a linearly increasing D.C. voltage ramp is imposed on the sensing electrode, with respect to a reference electrode, and a small D.C. pulse is superimposed on the ramp. The difference in current at the end of the pulse and before the pulse is utilized to determine the D.C. level at which a particular electroactive species, if present, can be detected.

Of interest as general background are a number of publications identified as follows:

Oldham et al., *Analytical Chemistry*, Vol. 38, No. 7, June 1966, pages 867-872; Klein et al., "Improved Differential Pulse Polarography", *Electroanalytical Chemistry and Interfacial Electrochemistry*, Vol. 61, No. 1, May 10, 1975, pages 1-9. Christie et al., "Constant Potential Pulse Polarography", *Analytical Chemistry*, Vol. 48, No. 3, March 1976, pages 561-564. Parry et al., "Evaluation of Analytical Pulse Polarography", *Analytical Chemistry*, Vol. 37, No. 13, December 1965, pages 1634-1637; and Schmidt et al., *Modern Polarographic Methods*, Academic Press, New York, N.Y. (1963). A number of electronic systems have been developed and disclosed which effect processing of signals developed from electrochemical detection cells, including the Letters Patent to David et al., supra. Examples of such systems are shown and discussed in U.S. Pat. Nos. identified as follows:

| U.S. Letters Pat. No. 3,420,764 | Schlein | January 7, 1969 |
| U.S. Letters Pat. No. 4,253,847 | Matson et al. | March 3, 1981 |
| U.S. Letters Pat. No. 4,321,322 | Ahnell | March 23, 1982. |

The known methods, techniques and systems may be characterized as providing a limited specificity and sensitivity.

SUMMARY OF THE INVENTION

An object of the present invention is to provide a method of gas detection using real time differential pulse detection (RDPD) which has improved specificity and sensitivity as compared to conventional voltammetry.

An additional object of the present invention is to provide an electronic system especially useful for carrying out the method.

Another object of the present invention is to provide an electrochemical detection cell which can readily be associated with and form part of the electronic system.

A further object is to provide an electronic system for detecting gas which can easily be carried about by an individual and can work in various orien- tations.

The improvements in specificity and sensitivity of the present invention in its various aspects are a result of two modifications of the prior art. First, the bias of the sensing electrode of a sensor is periodically pulsed, overcoming the mass transfer limitations which limited the sensitivity of prior art systems. Second, differential signal processing is used, rather than the D.C. processing used in prior systems, resulting in important specificity improvements. A major aspect of the present invention includes modification of the configurations of prior art sensors so they are compatible with pulsed electronics.

In its system aspect, these objectives are achieved in accordance with the present invention by providing a system which includes a conductive connection between a counter electrode of an electrochemical detection cell and the output terminal of a first operational amplifier, which has its inverting (−) input terminal conductively connected to the reference electrode of the cell. The inverting input terminal and the output terminal of the first operational amplifier may be capacitively connected to ensure amplifier stability. The other, a non-inverting (+) input terminal of the first operational amplifier is connected to a dynamic biasing network which provides an additive or subtractive D.C. pulse train, fed via a first analog switch, that is superimposed on the fixed-background-bias D.C. voltage. The dynamic biasing network includes adjustable potentiometers or voltage dividers, active circuit components and a first analog switch. The working or sensing electrode of the electrochemical detection cell is coupled, via a resistor, to the inverting (−) input terminal of a second operational amplifier, its other, non-inverting (+) input terminal being connected to a point of reference potential. The output terminal of the second operational amplifier is coupled to a buffered sample-and-hold circuit, which includes a storage capacitor and an analog switch, via a processing circuit. The processing circuit includes second and third analog switches conductively connected to respective storage capacitors which are coupled to respective inputs of a further operational amplifier, one via another operational amplifier. The four analog switches are operatively associated with a synchronized control circuit which opens and closes them in a predetermined sequence. As a result the further operational amplifier, which acts as a subtracting amplifier, produces a series of output pulses which are stored via a sample-and-hold buffering stage having its output coupled to an alarm circuit via a threshold comparator. Further data processing analog and/or digital may be provided from here.

In its apparatus (detection cell) aspect, the objects are achieved by providing an electrochemical detection cell which includes, in the order named, a stack of components constituted by a first membrane, an electrode carrier having reference and counter electrodes thereon, a membrane support, an electrode carrier having a sensing electrode thereon, and a permselective membrane. Whatman filter papers or layers of another inert hydrophilic insulator are positioned between the sensing electrode and both the counter and reference electrodes, these being positionable in a central rectangular opening of the membrane support. These components are operatively associated with structures which allow air or gas ambient to address the membranes, effect the application of an electrolyte to space between the electrodes by, for example, a wick which extends between an electrolyte-containing reservoir and the Whatman filter papers.

In its method aspect, the objects are achieved by providing an electrochemical detection cell having a sensing electrode, a counter electrode and a reference electrode, applying a fixed D.C. voltage bias to the reference electrode, superimposing at least one differential D.C. voltage pulse on the selected fixed D.C. voltage applied to the reference electrode, and determining difference between signals produced from the sensing electrode during a period before superimposing the differential D.C. voltage pulse and in a period before termination of the differential D.C. voltage pulse, while subjecting the sensing electrode to an environment in which the gas to be detected may be present.

The step of superimposing at least one differential D.C. voltage pulse train on the fixed D.C. voltage bias involves, in a preferred realization of the method, superimposing a first train of differential D.C. voltage pulses thereon, supplying a second train of pulses and a third train of pulses both synchronized with the first train of pulses and having the same repetition rate, and using respectively the second and the third train of pulses to control the sampling of signals from the sensing electrode in periods before start and before termination of each differential D.C. pulse of the first train, and determining the difference between the signals produced during the periods before the respective differential D.C. voltage pulses and those produced during the periods before termination of the respective differential D.C. voltage pulses.

BRIEF DESCRIPTION OF THE DRAWINGS

FIG.. 1A is a graphical representation of potential applied to a sensing electrode of a detecting cell plotted against time, illustrating conventional voltammetry as practiced in a laboratory.

FIG.. 1B is a graphical representative of signal currents plotted against sensing electrode potential of a detecting cell, illustrating conventional voltammetry as practiced in a laboratory.

DETAILED DESCRIPTION OF THE PREFERRED EMBODIMENTS

Before turning to the details of the present invention as illustrated, a few brief remarks are in order, reference being made to various of the drawing figures, to provide an understanding of the background of the invention in its system, apparatus and method aspects.

Real time differential pulse detection according to the present invention is a modification of differential pulse voltammetry (DPV). Both specificity improvements and sensitivity gains on the order of 1,000 times have been realized in analytical instruments where conventional voltammetry has been replaced with DPV for reasons mentioned below.

Figure 1A:
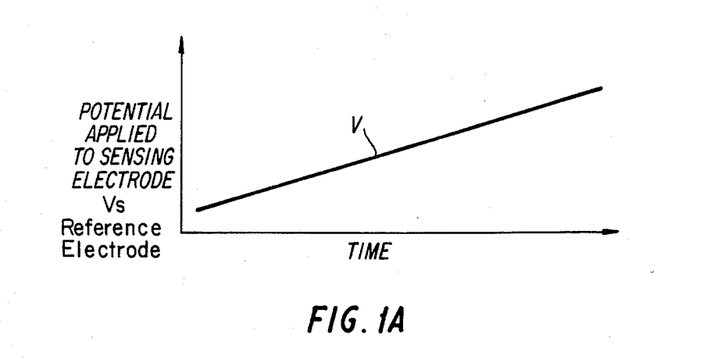
Figure 1B:
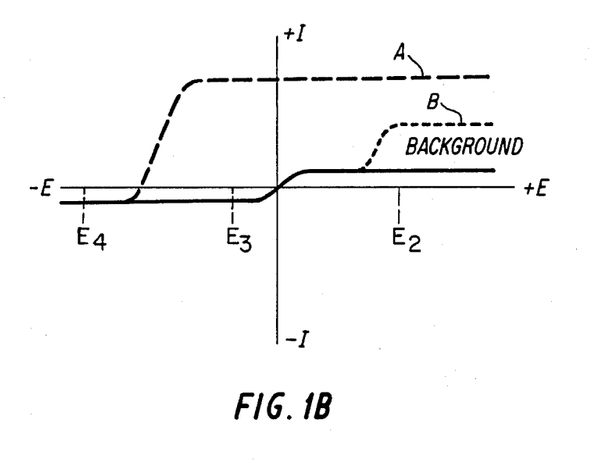

Analytical instruments utilizing conventional voltammetry maintain an accurate potential between the sensing and reference electrodes of an electrochemical sensing cell. The potential is increased linearly over time, as illustrated by line V in FIG. 1A. The current I, which is proportional to the concentration of any species reacting at the potential on the sensing electrode, is then plotted vs. the potential of the sensing electrode, as illustrated in FIG. 1B. Miniature detectors, which are sometimes carried by individuals, utilizing conventional voltammetry cannot scan the electrode bias due to the extremely large capacitive background currents that would develop at the high surface area gas sensing electrodes when its bias is scanned. Instead, the sensing electrode bias is set at a fixed potential slightly above that where the gas to be detected undergoes a redox reaction. The sensing electrode of a detector designed to detect gas B, as illustrated in FIG. 1B, would be set at $E_2$. The current at this point, minus the background, is proportional to the concentration of gas B in the air. The major drawback of this prior art technique is that all gases oxidized below $E_2$, that is at $E_3$ and $E_4$ for example, will act as interferents. For example, gas A will act as an interferent to gas B in this example. If gas B is a typical gas to be detected, there are a significant number of gasses which act like A in most environments.

Figure 2A:
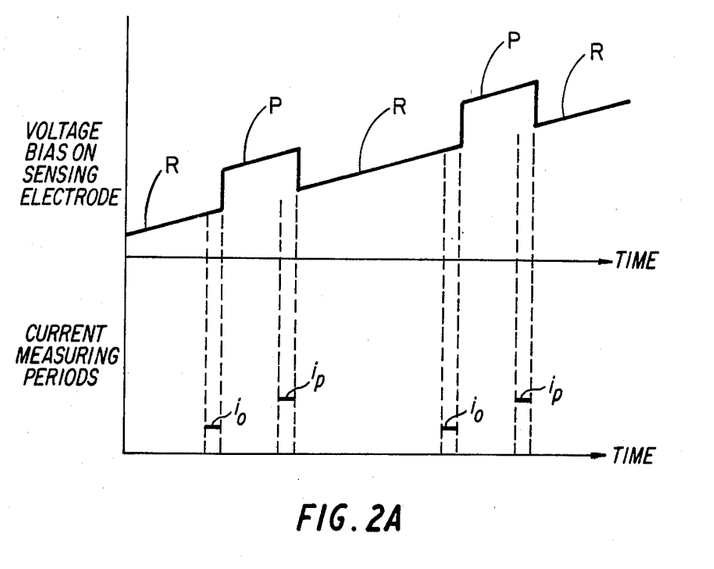
FIG. 2A is a graphical representation of the voltage bias applied to a sensing electrode of a detecting cell and current measuring periods plotted against time, illustrating differential pulse voltammetry again as practiced in a laboratory.
Figure 2B:
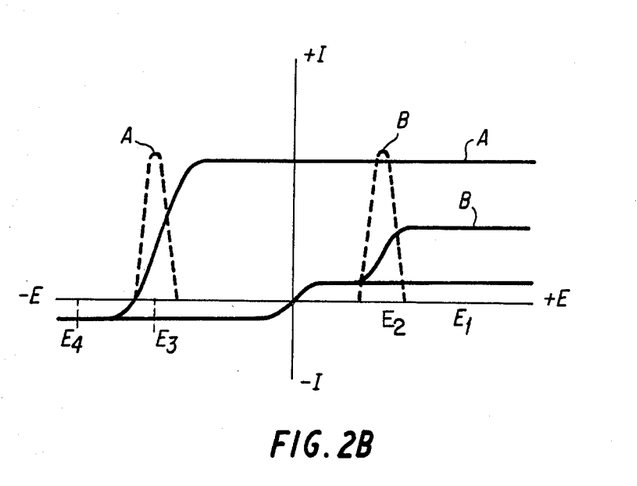
FIG. 2B is a graphical representation of signal currents plotted against sensing electrode potential of a detecting cell, illustrating differential pulse voltammetry as practiced in a laboratory.

In prior art laboratory differential pulse voltammetry, as illustrated in FIG. 2A, a series of small pulses P are superimposed on a linearly increasing voltage ramp R. The current is measured just before the individual pulses and just before the end of the individual pulses as illustrated, respectively, as $i_o$ and $i_p$. The DPV signal is the difference between the average current at the end of a pulse P and that before the pulse. Therefore, a current vs voltage plot for a DPV experiment yields a series of peaks instead of plateaus, as illustrated by the dashed lines in FIG. 2B. The peaks roughly coincide with the half wave potentials of conventional voltammetry. The specificity advantage of DPV becomes obvious when one examines FIG. 2B. The signal current at $E_2$ is proportional only to the background and gas B in the DPV mode. Gas A does not interfere since it is included in both the current before and at the end of the pulse. The signal current at $E_3$ has, in effect, been cancelled. The solid curves A and B, and the dashed curves A and B, in FIG. 2B represent respectively conventional and known DPV signals. The improvement in sensitivity is due to decreased concentration gradients at the electrode surface. The concentration gradient of the electroactive species at the electrode surface is the primary phenomenon limiting the sensitivity of most conventional voltammetry experiments. The concentration gradient is reduced in DPV, since the electroactive species is only depleted 20–300 milliseconds per second in a typical application.

The present invention involves RDPD, which in some respects is similar to DPV. The major difference between the two are that (1) the pulses are superimposed on a fixed bias in RDPD instead of a linearly increasing voltage ramp, and (2) the RDPD signals are continuously sampled, held, and updated. Real time signal monitoring is accomplished since the update process occurs after each pulse. The fixed bias would be set at a small voltage, typically from about 5 mv to about 100 mv, below $E_2$ in FIG. 2B in a RDPD detector designed to detect gas B. A pulse of from about 10 msec. to about 200 msec., for example, a 20 msec. pulse of approximately 20 mv would be, superimposed periodically on the continuous fixed bias, in accordance with the present invention. The RDPD signal would be equal to the difference between the average current during the last 2 to 50 msec. of the pulse minus the average current during the last 2 to 50 mesc. before the pulse. Detectors based on RDPD display most of the sensitivity and specificity advantages of analytical DPV instruments. In addition, the background signal deviation associated with temperature fluctuations of detectors based on conventional voltammetry are eliminated, since both sampled currents $i_o$ and $i_p$ will vary equally with temperature.

Figure 3:
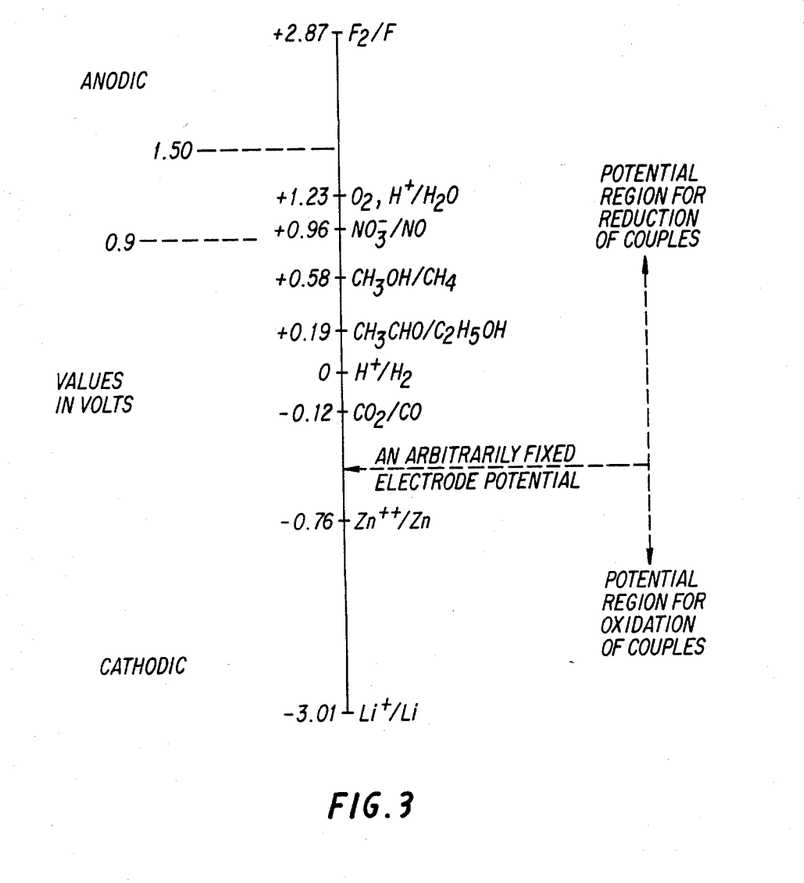
FIG. 3 is a chart derived from the electromotive series of elements indicating for exemplary redox couples theoretical relative electrode potentials determining whether a couple will undergo an oxidation or a reduction reaction.
Figure 5:
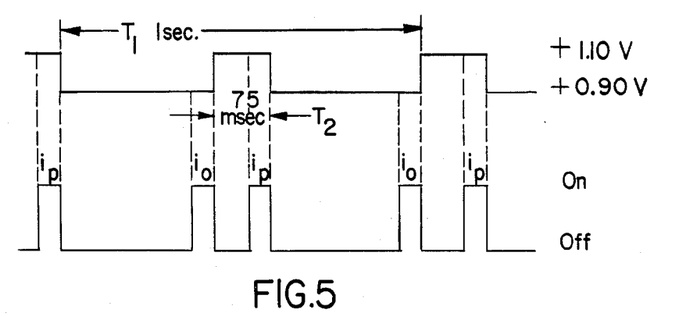
FIG. 5 is a graphical representation of an exemplary voltage bias applied to a sensing electrode of a detecting cell plotted against time, illustrating features of gas detection method using real time differential pulse detection in accordance with the present invention in its method aspect.

Referring to FIG. 3., which is known from the U.S. Pat. No. 3,776,832 to Oswin et al., supra, it is obvious that if one were to apply a potential of $+1.0$ V vs. the standard hydrogen electrode (SHE) to a voltametric cell in order to detect NO, $C_2H_5OH$ and CO may also be oxidized and act as interferents. In practicing the present invention, however, one would apply a fixed bias between the sensing and reference electrodes, for example $+0.90$ V as shown in FIG. 5, slightly lower then potential of the redox couple to be detected. A small additional pulse of approximately 0.20 V would be superimposed on the fixed potential such that the sum of the fixed potential and pulse would be greater than the half wave potential of the species to be detected (including overpotential). The current would be measured before each pulse and toward the end of each pulse as represented by $i_o$ and $i_p$, in FIG. 5. The output signal would be the difference between the two measures or $i_p - i_o$.

Since most interferents are oxidized equally at the fixed background bias B and the bias $B + P$, most interferents would not be included in the signal ($i_o - i_p$). Only substances oxidized between 0.90 V and 1.10 V would be oxidized if a pulse were applied. The sensitivity would also be increased through the utilization of the RDPD technique.

Figure 4:
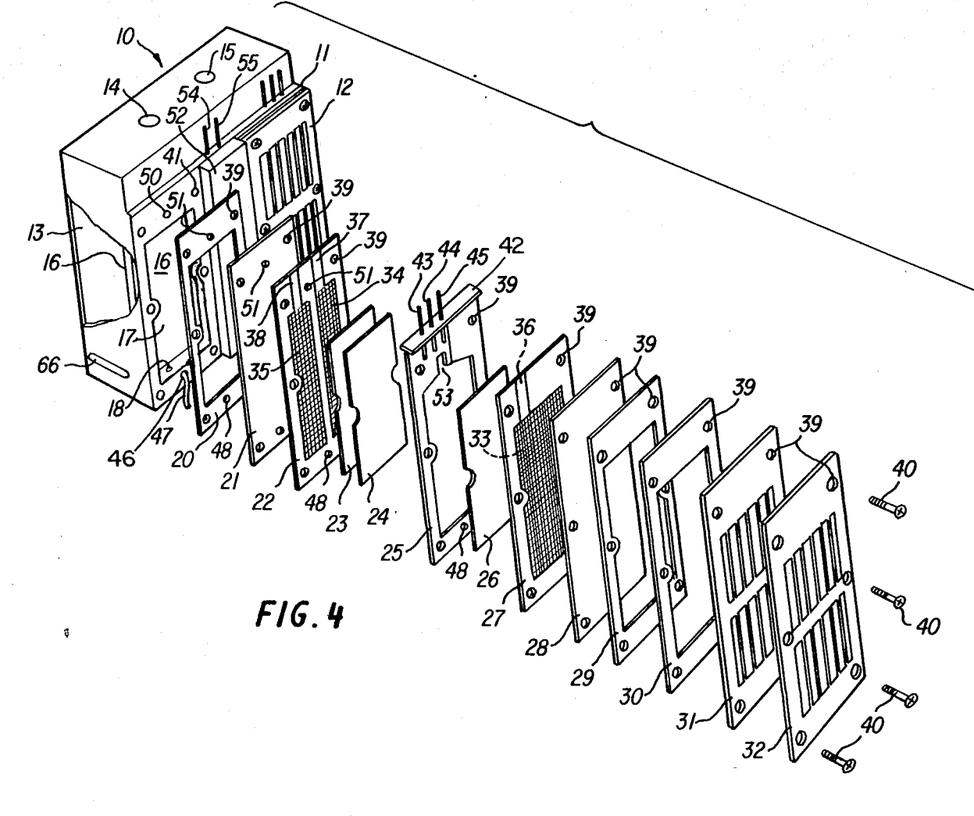
FIG. 4 is a pictorial view of a disposable module which incorporates two gas detecting electrochemical detection cells, one being shown exploded, constructed in accordance with the present invention and constituting the sensor of same in its system aspect.

A disposable module is illustrated in FIG. 4, the module including a pair of electrochemical detection cells constructed in accordance with the present invention. The two cells are operationally associated with a molded cell housing 10 made of a plastic, one of the cells 11 being shown fixed to the outside of the housing 10 by a plurality of screws 12. The other cell is shown for the purpose of illustration in an exploded configuration so as to show the relationship of its various components. It is to be understood that for most applications, a single cell would be provided and used. A pair of cells is provided for some applications.

A pair of electrolyte-containing reservoirs, only one reservoir 13 being visible through a broken away portion of a side wall, are provided within the cell housing 10. The reservoirs communicate with respective apertures 14, 15 which extend through a top portion of the housing 10 and allow one to place an appropriate electrolyte in the respective reservoirs. When the disposable module is being carried by a user or is in operation, it is to be understood that the apertures 14, 15 are closed by appropriate plugs. The reservoir 13 is defined in part by a wall 16, which is partially visible through a broken away portion of the side wall of the housing 10. The wall 16 also constitutes the back wall of an ambient chamber 17 having its bottom defined by a portion of the housing 10. The chamber 17 is in fluid communication with the atmosphere or other gaseous ambient via at least one aperture 18 which extends through the bottom of the housing 10. The aperture 18 is shown somewhat larger relative to other features for the sake of clarity, it may be constituted by an aperture having a diameter of 0.02 inch.

The exploded electrochemical detection cell, as shown in FIG. 4, includes a series of members held in stacked relationship over the chamber 17, when the cell is assembled for operation. The depth of chamber 17 is shown larger relative to other features for the sake of clarity. It may, in fact, be very shallow, for example, 0.1397 cm. (0.055 inch) in depth in a practical embodiment. It can be formed by a recess in a surface of the housing 10, the wall 16 being integral with the housing 10. The members include an apertured rectangular gasket 20 which is positioned about the open front of the chamber 17. The cell has, in the order named, in stacked relationship a polypropylene (PPE) membrane 21 which allows passage of $O_2$ while not allowing a large amount of interferent gases to pass, an electrode carrier 22 which may be realized as a porous polytetrafluoroethylene (PTFE) membrane or the like, two sheets of Whatman filter paper or another suitable hydrophilic insulator 23, 24, a membrane support 25, a further Whatman filter paper 26, an electrode carrier 27 which may be realized as a porous polytetrafluoroethylene (PTFE) or polypropylene membrane or the like, a permselective membrane 28 made, for example, of a molecular sieve or alumina impregnated with a reactive material such as potassium permanganate, an apertured rectangular gasket 29, a metal frame 30, and one or more grille members 31, 32. The membrane 28, when made as suggested above, is especially useful when one wishes to detect CO, while excluding passage of $H_2S$, alcohols and several other gases.

The electrode carrier 27 supports or is integral with a sensing electrode 33, the sensing electrode being preferably of a noble metal, for example, gold or of carbon, the noble metal or carbon being supported by and having been applied to a substrate of nickel or the like. The electrode 33 is desirably in the form of mesh or screen and could be a pure noble metal. The electrode carrier 22 supports a pair of spaced-apart electrodes 34, 35, these electrodes constituting respectively the reference electrode and counter electrode of the electrochemical detection cell of the present invention. The reference electrode 34 and counter electrode 35, like the sensing electrode 33, are preferably made of a noble metal, such as gold or platinum, or of carbon and have the form of a mesh or screen. Alternatively, the reference and counter electrodes could be composite electrodes fabricated from a finely divided conductive powder and an inert plastic binder, the conductive powder being, for example, metal or carbon powder. The reference electrode 34, the counter electrode 35 and the sensing electrode 33, because of their construction, present a large surface to the materials with which they come in contact, particularly the electrolyte and gas from the environment with which the sensing electrode 33 comes in contact with via the permselective membrane 28 and the grille members 31, 32. In order to provide electrical connections to the respective electrodes 33, 34 and 35, these electrodes are respectively provided with upwardly extending electrode portions 36, 37 and 38 and which may advantageously be extensions of the electrodes proper and be respective meshes.

Each of the stacked members 20-22, 25, and 27-32 are provided the vicinity of their edges with a plurality of the aligned apertures 39, six being shown for purposes of illustration for each, through which respective screws 40 are to extend, the housing 10 including a corresponding and aligned plurality of threaded bores 41 which are to receive the screws 40 when the components are in assembled condition.

The membrane support 25 is an insulating member and is provided on its upper-most edge with an insulating plate or extension 42 thereof which is fixed thereto or made integral therewith in a conventional fashion. Three, spaced-apart, electrical contacts 43, 44 and 45 extend upwardly from the insulating plate or extension 42 and through the insulating plate or extension 42 so as to provide respective contact areas beneath the insulating plate or extension 42 which contact respectively with the upwardly extending respective metal portions 38, 36 and 37 of the respective counter electrode 35, the sensing electrode 33 and the reference electrode 34, when the exploded cell is in its assembled condition. The contacts 43-45 are preferably made by the same conductive material as the portions 38, 36 and 37 of the electrodes and, if desired, may be fixed thereto by a conductive epoxy resin containing the same metals.

An aperture 46 extends through the housing 10 into the reservoir 13 and has therein a wick 47 which, when the members are assembled, extends through a passageway defined by respective aligned apertures 48 in the gasket 20, the membrane 21, the electrode support 22 and the membrane support 25 so as to supply electrolyte from the reservoir 13 to the Whatman filter papers 23, 24 and 26 between the sensing electrode 33 and the reference and counter electrodes 34, 35.

A further aperture 50 extends through the housing 10 and into the reservoir 13, the aperture 50 defining a passageway, when aligned with apertures 51 in the membrane 21 and the gasket 20, between the space between the electrodes 33, 34, 35 via a slot 53 in the top portion of the membrane support 25 to allow gas produced to move to reservoir 13 thereinto.

Figure 9:
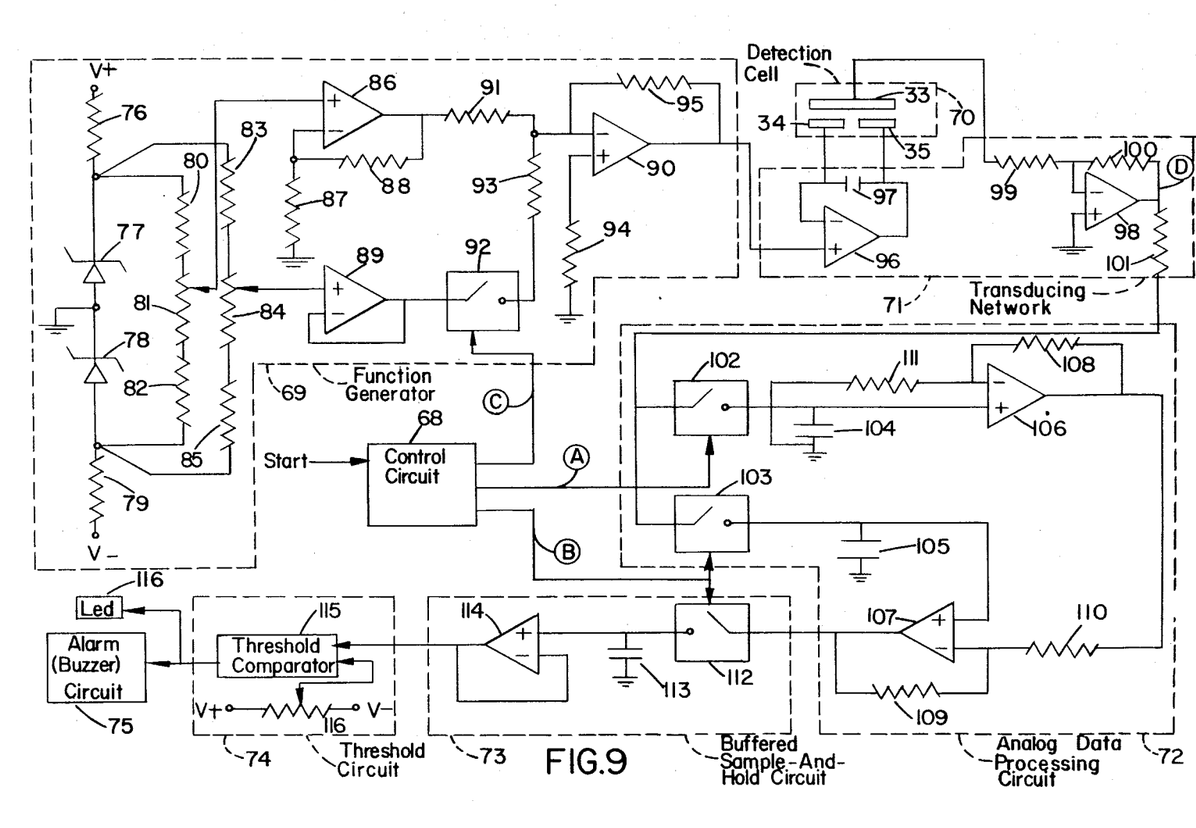
FIG. 9 is a simplified, schematic, block diagram of an electronic system for detecting gas using real time, differential pulse detection in accordance with an exemplary embodiment of the present invention in its system aspect.

As illustrated in FIG. 4, the disposable module includes between the two electrochemical sensing cells a portion shown as an elongated, longitudinal protrusion 52 which includes within it a battery for powering the electronic system of the present invention. The battery within the portion of the module behind the protrusion 52 is conductively connected to the electronic system of the present invention via electrical contacts 54, 55. The electronic portion of the invention, as illustrated in some detail in FIG. 9, is physically located on the top portion of the cell housing 10 and is electrically connected to the electrical contacts 43-45, 54 and 55. The contacts 54, 55 also are connected to supply power to a second electronic system located on the top portion of the housing 10 and which corresponds to that of FIG. 9.

but is set to detect a different gas or is present as a redundant system to assure a high degree of reliability, this second electronic system being associated with the cell 11 via three contacts (unnumbered) which correspond to the contacts 43-45.

Figure 6:
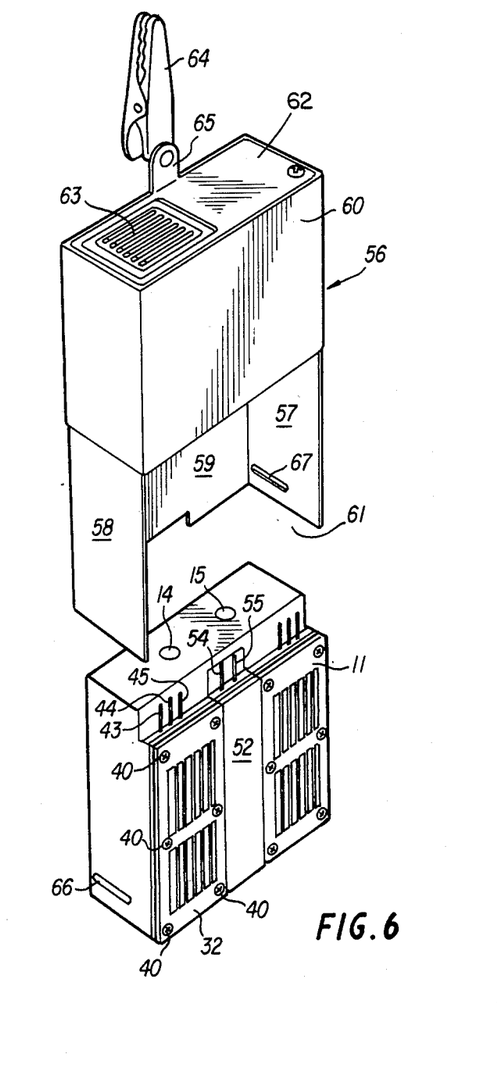
FIG. 6 is a pictorial view of the disposable module illustrated in FIG. 4 in association with a casing which also houses an alarm unit.

The cell housing 10, with its associated electrical contacts 43-45, and 54-55, is shown in FIG. 6, with the apertures 14, 15 being visible. The electronic system, including a small buzzer or other audible alarm, is carried within the casing generally designated by the numeral 56. The casing 56 includes a pair of side walls 57, 58, a backwall 59 and a front wall 60. The front wall 60 does not extend longitudinally to the same extent as the side walls 57, 58 and the back wall 59 so as to provide an opening 61 having a vertical extent such that when the disposable module housing 10 is inserted into the casing 56, the outermore grille member 32 of the one cell and the corresponding grille member of the other cell 11, as well as the protruding portion 52 of the cell housing 10 which contains the battery for the electronic system, will not be covered. The casing 60 is open at the bottom so that the cell housing 10 can be easily inserted into it from the bottom with its respective electrical contacts 43-45 and corresponding ones associated with the cell 11 and contacts 54, 55 coming into contact with appropriate connectors associated with the two respective electronic systems which are carried within the casing 60. The top wall 62 of the casing 56 includes a grill work 63, behind which an appropriate buzzer or audible alarm (not visible) for sounding an alarm signal is provided. An alligator clip 64 is fixedly connected with an upstanding tab 65 of the casing 56 so as to provide a means connecting the alarm unit, constituted by the casing 56 and the disposable cell module within it, to the shirt pocket or the like of a user. The cell housing 10 is removably held within the casing 56 by a pair of detents, only one detent 66 being visible on one of the side surfaces of the cell housing 10, a corresponding detent being and on its corresponding outwardly facing side surface, which is not visible. The detents 66 cooperate with a pair of detents which are present on opposed, inwardly facing side surfaces of the casing 56, only one groove 67 being visible.

The real time differential pulse detection (RDPD) sensor shown in FIG. 4 allows one to use the differential pulse technique to improve both the specificity and sensitivity of electrochemical cells adapted to detect various species in a gaseous environment. The construction of the sensor is similar to those described in the U.S. Letters Patents of Oswin et al., supra, and Stetter, supra, with the exception of the arrangement of parts and electrode differences; the metal electrodes 33-35 are configured in such a way to provide low resistance and a very low dual layer capacitance, are spaced close together. The sensing electrode 33 is sandwiched between a gas permeable membrane 28 and a hydrophilic insulator, in the form of Whatman filter papers 23, 24 and 26, soaked with the electrolyte, so the sensor can be operated in any orientation or during movement. The filter papers 23, 24 and 26 are positioned between the sensing electrode 33 and each of the reference electrode 34 and the counter electrode 35 allowing effective application of the electrolyte while maintaining close spacing. The polypropylene membrane 21 serves the purpose of protecting the reference electrode 34 from interferents. The metals preferably used to construct the sensing electrode 33 can be operated at much higher potentials than mercury, allowing one to detect both oxidizable and reducible gases, unlike the sensor disclosed in the Letters Patent to David et al., supra. One should desirably use concentrated solution of a strong acid or base or a salt as the electrolyte. Of course, these materials should be selected and used in such concentration taking into account expected operating conditions and safety factors, so as to assure that the materials will not precipitate out of solution while using a solution which is as concentrated as practicable. Among the many materials which can be used for the electrolyte are aqueous solutions of $H_2SO_4$, KOH and KCl.

Figure 7A:
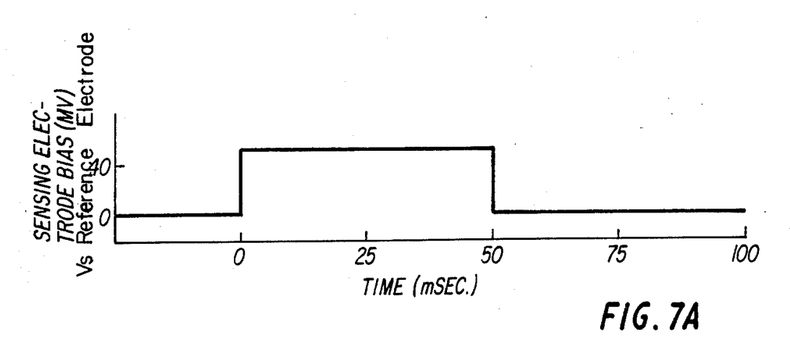
FIGS. 7A–7C are graphical representations respectively of sensing electrode bias, background current and faradaic current which is to flow in the sensor shown in FIG. 4 during operation thereof.
Figure 7B:
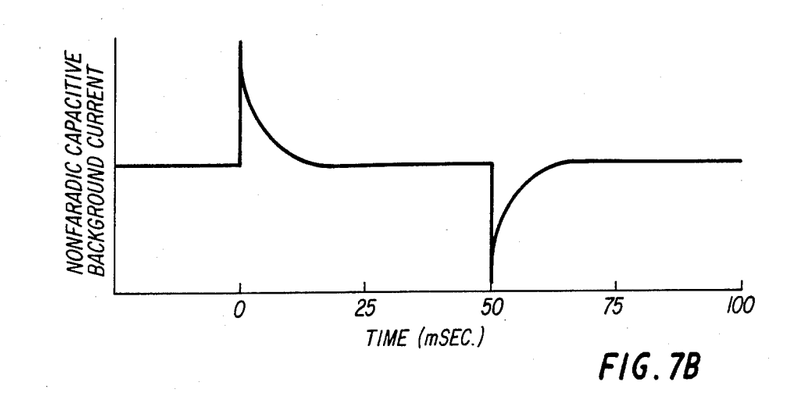
Figure 7C:
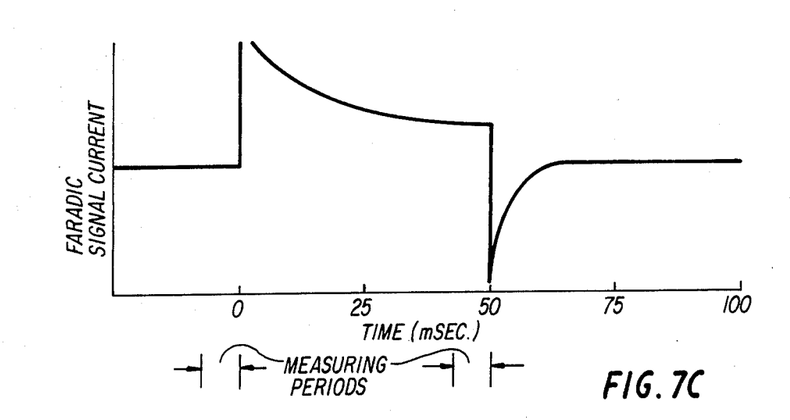

The advantages of the RDPD sensor become obvious after examining the two types of current which flow thru an electrochemical sensor operating in the RDPD mode. FIGS. 7A-7C depict characteristics of the RDPD sensor of the present invention in which cyanide is oxidized on a silver or gold sensing electrode. The sensing electrode potential with respect to the reference electrode is periodically pulsed from zero mV to 50 mV, as shown in FIG. 7A. Charging the sensing electrode to its new potential results in a positive spike at the beginning of each pulse and a negative spike at the end of each pulse, as shown in FIG. 7B. This current is governed by the following equation, Schmidt et al., supra:

$$i(t) = \frac{\Delta E}{R} \exp\left[\frac{-t}{RC}\right] \tag{1}$$

where
i(t)=background current at time t
$\Delta E$=bias pulse height
R=cell resistance
t=time after initiation of bias pulse
C=dual layer capacitance of the sensing electrode.

The capacitive background current occurs in both the absence or presence of the gas to be detected. If the gas to be detected is present, the Faradaic signal current shown in FIG. 7C is superimposed on the background capacitive current of FIG. 7B. The signal current is described by the following equation Parry et al., supra:

$$i(t) = nFAC\left[\frac{D}{t}\right]^{\frac{1}{2}}\left[\frac{\sigma - 1}{\sigma + 1}\right] \tag{2}$$

where
i(t)=agent signal current at time t
n=number of electrons transferred per molecule of gas
F=Faraday's constant
A=sensing electrode active area
C=agent concentration in the electrolyte adjacent to the electrode
D=diffusion coefficient of the agent in the electrolyte
t=time after initiation of the pulse
$\sigma = \exp(nF\Delta E/2RT)$
$\Delta E$=DPV bias pulse height
R=gas constant
T=temperature (K).

The DPV signal is the difference current, that is $i_p - i_o$. Therefore most interferents are removed when the electronics system subtracts $i_p - i_o$.

Gas sensors described to date, such as those cited in U.S. Letters Patents to Oswin et al., supra, and to Stetter, supra, are unsuitable for use in the FDPV mode for several reasons. The primary reason involves poor sensitivity due to the nature of the gas sensing electrodes described in the literature. Equation (2), supra, states that the signal level is inversely proportional to the square root of the time after the pulse begins. Since the signal is measured at the end of the pulse, maximum sensitivity is achieved by minimizing the pulse width. The minimum size of the pulse width is determined by the time required for the capacitive background current to decay, since it masks the Faradaic gas signal until it decays to nearly zero. Unfortunately, electrodes used in prior art gas sensors exhibit a very slow background current decay, which severaly limits their sensitivity. Their extraordinary large electrode surface area cause a slow background current decay due to the large R and C terms in equation (1), supra.

The background current problem of prior art electrodes used in the RDPD mode is overcome in this invention by using noble metal screen electrodes or the like and placing them in relation to the other parts as described above. This decreases the R and C terms described in equation (1), supra, of the sensor several orders of magnitude, and results in the improvement in the background signal shown in FIG. 8C as compared to the standard background current shown in FIG. 8B. The background signal improvement allows one to utilize shorter pulses, which increases the sensitivity as described in equation (2).

Figure 8A:
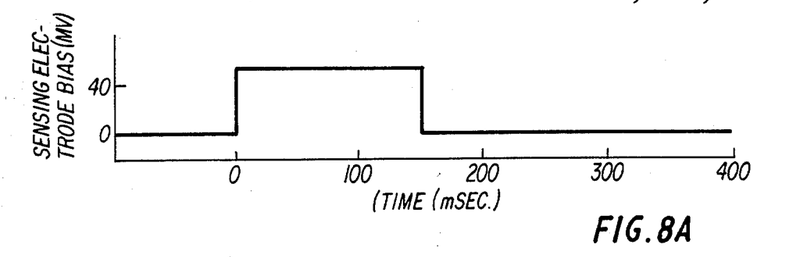
FIGS. 8A–8C are graphical representations respectively of sensing electrode bias, standard prior art sensor electrode background current and background current in the sensor shown in FIG. 4.
Figure 8B:
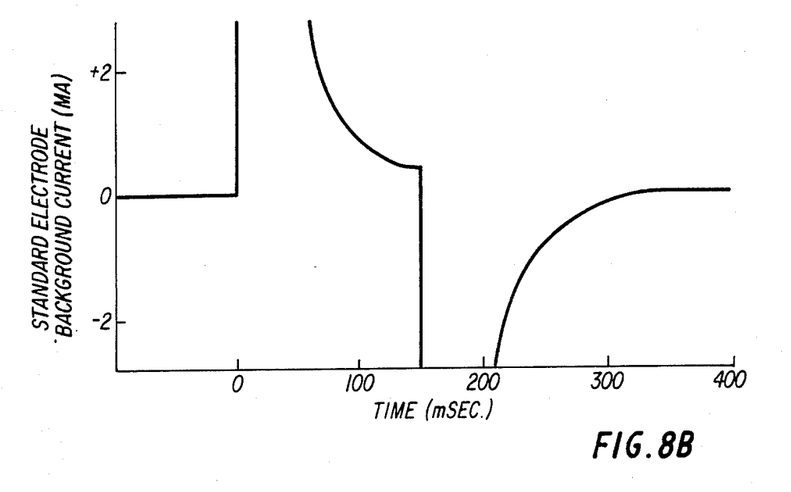
Figure 8C:
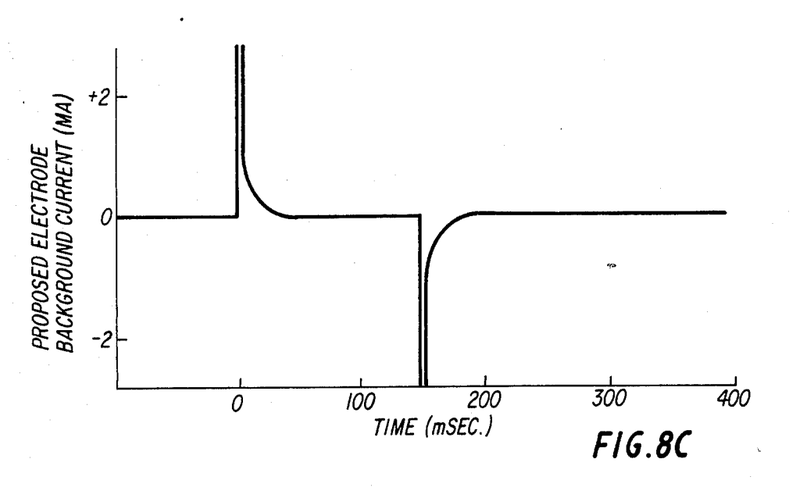

The use of the proposed waveform shown in FIG. 8A instead of the prior art waveform shown in the U.S. Letters Patent to David et al., supra, enhances sensitivity in two ways. First, the shorter pulse allows measurement of the gas signal before it has decayed to the degree in the U.S. Letters Patent to David et al., supra. Second, the short pulse, typically about 50 msec. long, is only repeated once every second (50 msec. on-950 msec. off), in contrast to the 200 msec. on-200 msec. off cycle used in the prior art. It has been established in the literature that the sensitivity decreases as the pulse on-off ratio increases.

In FIG. 9, a suitable, exemplary electronic system for real time, differential pulse detection, which is particularly useful when operably associated with the detection cell shown in FIG. 4 is illustrated. The real time, differential pulse detection electronic system, as illustrated in FIG. 9 includes a control circuit 68 having three syncronizing outputs, a function generator 69 responsive to one output from the control circuit 68 and having one output, a detection cell 70, which corresponds to the cell shown in exploded configuration and FIG. 4, and a transducing network (potentiostat) 71 which generates voltage and/or current signals proportional to the amount of agent reacting at the sensing electrode 33. The output from the transducing network 71 is coupled to an analog processing circuit 72, which is controlled by two of the output from the control circuit 68, and has its output coupled to a buffered, sample-and-hold circuit 73. The output from the sample-and-hold circuit 73 is fed to a threshold circuit 74 which, in turn, has its output fed to an audible alarm circuit 75 which may be constituted by a buzzer, and to a visible alarm circuit 116, which may be constituted by a light-emitting-diode (L.E.D.).

In a practical embodiment, the control circuit 68, the function generator 69, the transducing network 71 and the analog processing circuit 72 may be realized as a miniaturized circuit which can be positioned adjacent to a top portion of the cell housing 10 (FIG. 4) and in electrical connection with contacts 43-45 and 54,55 (FIG. 4), while the buffered, sample-and-hold circuit 73, the alarm circuits 75 and 116, and the threshold circuit 74 are desirably carried separately within the casing 56 (FIG. 6). It is to be appreciated that the output of a second analog processing circuit, associated with the second detecting cell 11 (FIG. 4), could have its output also connected to the buffered, sample-and-hold circuit 73 which would serve to sound the alarm circuit 75 and energize the alarm 116 were either system to produce an output from the respective analog processing circuits. Of course, the buffered, sample-and-hold circuit 73, the alarm circuit 75 and the threshold circuit 74 could be realized as part of a single disposable unit with the control circuit 68, the function generator 69, the transducing network 71 and the analog processing circuit 72 were a single real time differential pulse detection system, rather than two such systems, utilized.

The power for the circuit illustrated in FIG. 9 is obtained from a battery pack (not illustrated) which includes a ground midpoint, a V+ voltage terminal and a V− voltage terminal. A 4K ohm resistor 76, a first voltage reference 77, a second voltage reference 78 and a 4K ohm resistor 79 are connected in series with one another in the order named between the V+ and the V− terminals, the reference point (ground) being provided between the anode and cathode of the respective voltage references 77 and 78. The voltage references 77 and 78 provide for a constant steady D.C. voltage across the same. A first voltage divider, constituted by the series connection of a 1K ohm resistor 80, a 10K ohm potentiometer 81 and a 1K ohm resistor 82 connected in series, is connected across the voltage references 77, 78. A second voltage divider constituted by the series connection of a 1K ohm resistor 83, a 10K ohm potentiometer 84 and a 1K ohm resistor 85 is connected in parallel with the voltage references 77, 78. The wiper of the potentiometer 81 is connected to the non-inverting (+) terminal of an operational amplifier 86, arranged in a non-inverting amplifier, which has its inverting (−) terminal connected to ground via a 10K ohm resistor 87 and its output terminal connected to its inverting terminal via a 20K ohm resistor 88. The operational amplifier 86, with its associated circuit components, is configured to buffer and to amplify the voltage supplied from the potentiometer 81.

The wiper of the potentiometer 84 is connected to the non-inverting (+) terminal of an operational amplifier 89 which is connected as a unity gain buffer and has its output terminal directly connected to its inverting terminal.

Figure 10:
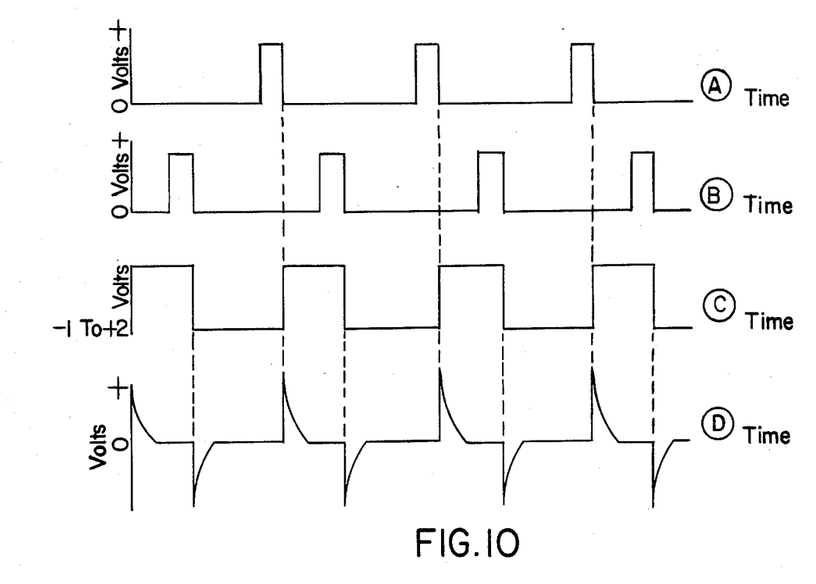
FIG. 10 is constituted by a series of graphical representations of waveforms at various points in the electronic system shown in FIG. 9, these representations being helpful in understanding the operation thereof.

The output terminals of the operational amplifiers 86 and 89 are coupled to the inverting (−) terminal of a further operational amplifier 90 arranged as a summing, inverting amplifier, the output terminal of the operational amplifier 86 being connected via a 10K ohm resistor 91, while the output terminal of the operational amplifier 89 is connected via a series connection of a controlled analog switch 92 and a 10K ohm resistor 93. The non-inverting (+) terminal of the operational amplifier 90 is connected to ground via a 5K ohm resistor 94 and its output terminal is connected to its inverting input terminal via a 10K ohm resistor 95. A synchronized output from the control circuit 68, having the form of the waveform illustrated as waveform C in FIG. 10, is coupled to the enabling input of the analog switch 92.

The final stage, operational amplifier 90, of the function generator 69 has its output terminal connected directly to the non-inverting (+) input terminal of an operational amplifier 96, the first stage of the transducing network (potentiostat) 71. The output terminal of the operational amplifier 96 is connected to the counter electrode 35 of the detection cell 70. The inverting (−) input terminal of the operational amplifier 96 is connected to the reference electrode 34 of the detection cell 70. The output and inverting input terminals of the operational amplifier 96 being coupled together via a 0.1 $\mu f$ capacitor 97, so as to reduce the possiblity of the operational amplifier 96, and its associated circuitry undesirably going into oscillation.

The detection cell 70, as illustrated in FIG. 9, includes a sensing electrode 33, which is also shown in FIG. 4, is coupled to the inverting (−) terminal of an operational amplifier 98, via a 33 ohm resistor 99 which provides noise reduction. The non-inverting (+) terminal of the operational amplifier 98 is connected to ground, the output terminal thereof being connected to its inverting (−) input terminal via a 2.2K ohm resistor 100. The resistor 100 can be considered, in association with the other circuit components connected to the operational amplifier 98, to effect a current-to-voltage conversion, the resistor 100 determining the conversion gain. The output terminal of the operational amplifier 98 is connectd via a 5K ohm resistor 101, to the respective input terminals of controlled analog switches 102 and 103, which are the input stages of the analog processing circuit 72. The respective controlling inputs to the analog switches 102 and 103, are obtained from the control circuit 68 via connections thereto, the respective controlling inputs being constituted by signals corresponding to the waveforms shown in FIG. 10 as letter A and letter B, respectively. The respective output terminals from the analog switches 102, 103 are respectively connected to the ungrounded side of 0.1 $\mu f$ capacitors 104 and 105. The opposite plates of the capacitors 104 and 105 being connected to ground. The ungrounded sides of the respective capacitors 104, 105 are connected respectively to the non-inverting (+) input terminals of respective operational amplifiers 106 and 107, the respective output terminals and inverting (−) input terminals of the respective amplifiers 106 and 107 being connected via respective 22K ohm resistors 108 and 109. The output terminal of the operational amplifier 106 is connected to the inverting (−) input terminal of the operational amplifier 107 via a 22K ohm resistor 110. The inverting (−) input terminal of the operational amplifier 106 is connected to ground via a 22K ohm resistor 111.

The output terminal of the operational amplifier 107, which constitutes the output from the analog processing circuit 72, is connected to a controlled analog switch 112 which forms the input stage of the buffered, sample-and-hold circuit 73. The enabling input to the controlled analog switch 112 is obtained from the control circuit 68 via the connection thereto which also provides the same enabling input signal to the controlled analog switch 103, this signal being shown as a waveform B in FIG. 10. The output from the analog switch 112 is fed to the unground plate of a 0.1 $\mu f$ capacitor 113, its other plate being grounded. The capacitor 113 has its ungrounded plate connected to the non-inverting (+) input terminal of an operational amplifier 114, the inverting (−) input terminal of the operational amplifier 114 being directly connected to the output terminal thereof, which constitutes the output from the buffered, sample-and-hold circuit 73. The output terminal from the operational amplifier 114 is connected to a first input terminal of a threshold comparator 115 which has its other input terminal connected to a wiper of a potentiometer 116 which, as shown, is connected between the V+ and V− terminals of the battery pack power source. The potentiometer 116 could be connected in parallel with the voltage references 77, 78 for better regulation. The output from the threshold comparator 115, which constitutes the output of the threshold circuit 74, is connected to the audible alarm circuit 75, illustrated as a buzzer. The output of the threshold comparator 115 is also fed to a visible alarm circuit 117, illustrated as a light emitting diode (L.E.D.) 116 which may be powered from a switched power source or in some cases, an oscillator which would cause the L.E.D. 116 to blink on and off. The operational amplifiers 86, 89, 90, 96, 98, 106, 107 and 114 can be realized from respective one-quarters of two quad CMOS OP AMPS e.g. Intersil's ICL 7641 circuit modules.

Referring further to FIG. 9, reference being made additionally to FIG. 10, a brief discussion of the set up and operative sequence of the present invention is to be discussed. The user first determines which gas is to be detected, and selects the appropriate electrolyte which is placed in the electrolyte reservoir 13 (FIG. 4). This electrolyte, because of the wick 47 which extends from the reservoir 13 and to physical contact with the Whatman filter papers 23, 24 and 26 (FIG. 4), transfers some electrolyte into space between the sensing electrode 33 and each of the counter electrode 35 and the reference electrode 34.

One then selects, before placing the system into field operation, an appropriate fixed D.C. voltage bias by suitably adjusting the wiper of the potentiometer 81 so that the D.C. voltage at the non-inverting input to the operational amplifier 86 in FIG. 9 has a selected steady level which results in a steady, given D.C. voltage appearing on the inverting input terminal of the operational amplifier 90, which has its output directly connected to the non-inverting input terminal of the operational amplifier 96. The output terminal of the operational amplifier 96 and its inverting input terminal are directly respectively connected conductively to the counter electrode 35 and the reference electrode 34 of the detection cell 70, as pointed out above. One then selects the magnitude of the differential D.C. pulse which is to be superimposed on a representation of the fixed-background-bias D.C. by adjusting the wiper of the potentiometer 84. One may also set the sensitivity of the system by adjusting the wiper of the potentiometer 116 of the threshold circuit 74 so that a given output from the buffered, sample-and-hold circuit 73 must be present before the alarm circuits 75 and 116 respond. The system is then ready for operation under the control and synchronism of the control circuit 68 which may be realized as a timing circuit which includes a master oscillator, counters and logic circuits, so as to produce the appropriate control pulses, shown as waveform A-C in FIG. 10, in timed, synchronized sequence.

The control circuit 68, when turned on by user as suggested by the START input produces a train of short, for example ten msec. pulses, the pulses being shown as waveform A in FIG. 10, the individual pulses acting to enable the analog switch 102 which, when enabled, effects a transfer of the output signal from the operational amplifier 98 of the transducing network 71 to charge the storage capacitor 104 during the duration of the enabling pulse. This results in a voltage across the capacitor 104 which corresponds to the current produced from the transducing network 71 which responds to output from the sensing electrode 33 (FIGS. 4, 9) the detection cell just prior to the superposition of the differential D.C. pulse on the aforementioned and already present fixed-background-bias D.C. voltage fed to the inverting input terminal of the operational amplifier 90 and provided from the operational amplifier 86. In timed relationship with the individual pulses shown in waveform A in FIG. 10, the pulse control circuit 68 produces, at the trailing edge of each of these pulses, respective control pulses of, for example, 40 msec. lengths having the waveform C illustrated in FIG. 10 which enables the analog gate 92, causing a representation of the D.C. voltage output from the operational amplifier 89 to be superimposed on the fixed-background-bias D.C. potential output from the operational amplifier 86 as set by the placement of the wiper of the potentiometer 81. As a result, the reference electrode 34 exhibits an increase in voltage thereof for the duration of the individual control pulses illustrated as waveform C in FIG. 10. About 10 msec. before the respective enabling pulses applied to the analog switch 92 ends, the control circuit 68 produces a further 10 msec. enabling pulse which is applied to the respective analog switches 103 and 112 so as to enable these respective analog switches and in effect, transfer the difference between the stored signals appearing across the capacitors 104 and 105 to the buffered sample-and-hold circuit 73 via the operational amplifier 107 and, in particular, to the capacitor 113.

As pointed out above, the capacitors 104 and 105 are identical in size, therefore the respective voltages which appear on these respective capacitors correspond respectively to currents produced from the transducing network 71 which respectively correspond to the voltages produced from the detection cell 70 just before the beginning and just before the end of each of the pulses shown in FIG. 10 as waveform C and which are used to enable the analog switch 92.

The signals from the operational amplifier 107 are thus periodically stored on the capacitor 113 and the production thereof, at least over a given special level, indicates the presence of an agent to be detected, such as a gas, and which has been detected by the detection cell 70. The buffered, sample-and-hold circuit 73, in effect, holds the highest level it receives from the operational amplifier 107, which output is fed to the operational amplifier 114 which has its output coupled to the threshold circuit 74, in particular, to one input of the threshold comparator 115, which has its other input connected to the adjustable threshold level setting potentiometer 116. Whenever the output from the operational amplifier 114 exceeds the voltage supplied from the potentiometer 116, the threshold comparator 115 provides an output which enables the alarm circuits 75 and 116 or one of them if only one is present, these alarm circuits being shown as a buzzer and an L.E.D. In instances where the L.E.D. alarm circuit 116 is provided, it is turned on by an output from the threshold comparator 115, blinking in the case an oscillator is used to supply the power to the L.E.D. via a controlled switch (not shown) responsive to output from the threshold comparator 115. The output from the amplifier 114 could be used alternatively or in addition to effecting the turning on of the alarm circuits 75 and 116, to provide a direct analog readout to a meter or the like or be associated with digital storage and/or display and/or further processing.

It is to be understood that the foregoing description, and accompanying illustrations have not been set by way of limitation, but by way of example. It is to be appreciated that numerous other embodiments and variants are possible, without departing from the scope and spirit of the present invention, its scope being defined by the appended claims.

What is claimed is:

1. A system for detecting a gas in an environment comprising an electrochemical detection cell having a reference electrode, a counter electrode and a sensing electrode; said reference electrode and said counter electrode spaced apart from each other and from said sensing electrode, an electrolyte in contact with said reference electrode, counter electrode and sensing electrode, a membrane having a first surface exposed to said environment for passing said gas in said environment through said membrane to said sensing electrode, an operational amplifier having an output terminal, an inverting input terminal and a non-inverting input terminal, said output terminal being coupled to said counter electrode, said reference electrode being coupled to one of said input terminals; means for applying a fixed D.C. voltage bias to the other of said input terminals; means for applying at least one differential D.C. voltage pulse to said other input terminal to superimpose same on said fixed D.C. voltage bias to provide a corresponding differential D.C. voltage pulse on its output terminal, and means coupled to said sensing electrode and responsive to current therefrom for determining difference in Faradaic currents produced during a period before application of the differential D.C. voltage pulse and a period before termination thereof as an indication of presence of a given gas.

2. A system according to claim 1, wherein said reference electrode is coupled to said inverting input terminal of said operational amplifier, and said means for applying a fixed D.C. voltage bias and said means for applying a differential D.C. voltage pulse are coupled to said non-inverting input terminal.

3. A system according to claim 2, further including means for adjustably setting the fixed D.C. voltage bias.

4. A system according to claim 3, including means for adjustably setting amplitude of said differential D.C. voltage pulse.

5. A system according to claim 2, further including means for adjustably setting the amplitude of said differential D.C. voltage pulse.

6. A system according to claim 1, wherein said means coupled to said sensing electrode and responsive to current therefrom includes first storage means for storing a signal representative of current from said sensing electrode during a period before application of said differential D.C. voltage pulse and second storage means for storing a signal representative of current from said sensing electrode during a period before termination of said D.C. voltage pulse.

7. A system according to claim 6, wherein said first storage means and said second storage means comprise respective first capacitance means and second capacitance means, the signals being voltage signals.

8. A system according to claim 6, including means coupled to said first storage means and to said second storage means and responsive to the signals therefrom for determining the difference therebetween.

9. A system according to claim 8, wherein said first storage means and said second storage means comprise respective first capacitance means and second capacitance means, the signals being voltage signals.

10. A system according to claim 8, including alarm means, said alarm means being coupled to said means coupled to said first storage means and to said second storage means.

11. A system according to claim 10, including sample-and-hold circuit means for holding the highest signal representing the difference current, said sample-and-hold circuit means being coupled between said means coupled to said first storage means and to said second storage means, and said alarm means.

12. A system according to claim 10, wherein said alarm means comprises means for producing an audible signal.

13. A system according to claim 12, wherein said alarm means comprises means for producing a visual signal.

14. A system according to claim 10, wherein said alarm means comprises means for producing a visual signal.

15. A system according to claim 1, wherein said electrochemical detection cell comprises at least one further membrane positioned between said counter electrode and a gas-containing chamber and between said reference electrode and the gas-containing chamber.

16. A system according to claim 1, wherein said reference electrode, said counter electrode and said sensing electrode are meshes.

17. A system according to claim 1, wherein said sensing electrode is a mesh and said reference electrode and said counter electrode are composite electrodes.

18. A system according to claim 17, wherein said composite electrodes are of finely divided conductive powder and an inert plastic binder.

19. A system for detecting a gas in an environment comprising an electrochemical detection cell having a reference electrode, a counter electrode and a sensing electrode, said reference electrode and said counter electrode spaced apart from each other and from said sensing electrode an electrolyte in contact with said reference electrode, counter electrode and sensing electrode, a membrane having a first surface exposed to said environment for passing said gas in said environment through said membrane to said sensing electrode, means for applying a fixed D.C. voltage bias to said counter electrode for supplying electrical current through said electrolyte to said sensing electrode to maintain a predetermined potential at said reference electrode, means for superimposing at least one differential D.C. voltage pulse on said fixed D.C. voltage bias, and means coupled to and responsive to Faradaic signals from said sensing electrode for determining the difference between Faradaic signals produced during a period before the at least one differential D.C. voltage pulse is superimposed on the fixed D.C. voltage bias and during a period before termination of the at least one differential D.C. voltage pulse.

20. A system according to claim 19, wherein said means for superimposing at least one differential D.C. voltage pulse comprises means for superimposing a first train of differential D.C. voltage pulses on the fixed D.C. voltage bias, and said means responsive to signals from the sensing electrode includes: (1) means for producing a further train of pulses and an additional train of pulses both synchronized with the first train of pulses and having the same repetition rate and being timed to effect sampling of signals from the sensing electrode in periods before start and before termination of each differential D.C. pulse of the first train and (2) means responsive to the sampled signals for determining the difference between those produced during the periods before the respective differential D.C. voltage pulse and those produced during the periods before termination of the respective differential D.C. voltage pulses.

21. A system according to claim 20, including sample-and hold circuit means for storing the difference signal.

22. A system according to claim 20, including at least one alarm circuit responsive to the difference signal.

23. A method for detecting a gaseous agent in an ambient with an electrochemical detection cell having a sensing electrode, a counter electrode and a reference electrode, said reference electrode and said counter electrode spaced apart from each other and from said sensing electrode and having an electrolyte in contact with said reference electrode, counter electrode and sensing electrode, comprising the steps of exposing said ambient to one side of a membrane capable of passing said gaseous agent, exposing said sensing electrode with the gas passing through said membrane, applying a fixed D.C. voltage bias to the counter electrode for supplying electrical current through said electrolyte to said sensing electrode to maintain a predetermined potential at said reference electrode, superimposing at least one differential D.C. voltage pulse on the fixed D.C. voltage bias and determining the difference between Faradaic signals produced from the sensing electrode during a period before superimposing the differential D.C. voltage pulse and in a period before termination of the differential D.C. voltage pulse.

24. A method according to claim 23, wherein the step of superimposing at least one differential D.C. voltage pulse on the fixed D.C. voltage bias involves superimposing a first train of differential D.C. voltage pulses thereon, supplying a second train of pulses and a third train of pulses both synchronized with the first train of pulses and having the same repetition rate, and using respectively the second and the third train of pulses to affect sampling of signals from the sensing electrode in periods before start and before termination of each differential D.C. pulse of the first train, and determining the difference between the signals produced during the periods before the respective differential D.C. voltage pulses and those produced during the periods before termination of the respective differential D.C. voltage pulses.

* * * * *